United States Patent [19]
Barreras, Sr. et al.

[11] Patent Number: 5,949,632
[45] Date of Patent: Sep. 7, 1999

[54] POWER SUPPLY HAVING MEANS FOR EXTENDING THE OPERATING TIME OF AN IMPLANTABLE MEDICAL DEVICE

[75] Inventors: Francisco Jose Barreras, Sr., Miami Beach; Guillermo Echarri; Roberto Echarri, both of Miami, all of Fla.

[73] Assignee: Exonix Corporation, Miami, Fla.

[21] Appl. No.: 09/203,275

[22] Filed: Dec. 1, 1998

[51] Int. Cl.⁶ .............................. H02H 3/20; H02H 7/10
[52] U.S. Cl. ................................. 361/90; 363/50
[58] Field of Search ................................. 363/50; 361/18, 361/54, 56, 90; 307/116, 126, 130; 607/33, 61

[56] References Cited

U.S. PATENT DOCUMENTS

| | | | |
|---|---|---|---|
| 4,884,242 | 11/1989 | Lacy et al. | 365/229 |
| 5,807,397 | 9/1998 | Barreras | 607/61 |
| 5,831,351 | 11/1998 | Khosrowpour et al. | 307/139 |

*Primary Examiner*—Matthew Nguyen
*Attorney, Agent, or Firm*—Thomas R. Vigil

[57] ABSTRACT

A power supply comprising: a power source including a capacitive, nuclear or an electrochemical device for storing electrical energy; sensing circuitry for sensing when the voltage on power source is above or below a certain level; a DC-DC converter coupled to the power source switching circuitry coupled to the sensing circuitry and operable to connect the DC-DC converter to an output load and disconnect the power source from the output load when the voltage on the power source falls below a certain level and for connecting the power source to the output load and disconnecting the DC-DC converter from the output load when the voltage on the power source rises above a certain level; circuitry for activating the DC to DC Converter when the voltage on the power source falls below a certain level; and circuitry means for shutting down the DC to DC Converter when the voltage on the power source rises above a certain level.

The method for extending the operating time of a capacitive, nuclear or electrochemical power source includes the steps of: sensing when the voltage level on the power source is below or above a certain level; producing a first logic signal when the voltage on the power source falls below a certain level and producing a second logic signal when the voltage on the power source is above a certain level; providing a DC-DC converter coupled to the output of the power source; switching the connections to an output load from the power source to the DC-DC converter when the first logic signal is produced; connecting the power source to an output load and disconnecting the DC-DC converter from the output load when the second logic signal is produced; activating the DC to DC Converter when the first logic signal is produced; and shutting down the DC to DC Converter when the second logic signal is produced.

18 Claims, 6 Drawing Sheets

POWER SUPPLY HAVING MEANS FOR EXTENDING THE OPERATING TIME OF AN IMPLANTABLE MEDICAL DEVICE

BACKGROUND OF THE INVENTION

1. Field of the Invention

The present invention relates to a method and circuitry for extending the operating time of a capacitive, electrochemical or nuclear power source in an implantable medical device, by activating a step-up DC to DC Converter upon sensing that the power source voltage has decreased to the minimum operating voltage required by the medical device.

2. Description of the Prior Art

A number of new, state-of-the-art, implantable medical devices, such as, a neural stimulator, a pacemaker, a defibrillator, a drug infusion pump, to name a few, are powered by either a rechargeable or a non-rechargeable power source. This power source can be either a large value capacitor, a rechargeable or a non-rechargeable electrochemical cell, or a nuclear cell. One limitation of all these power sources is that eventually their voltage will diminish to the minimum operating voltage required by the electric circuit at which point the device will cease to provide medical therapy. However, there may be a significant electric charge remaining in the power source that cannot be utilized due to limitations imposed by the minimum operating voltage.

SUMMARY OF THE INVENTION

The present invention relates to implantable medical devices powered by an electrical power source, such as a large value capacitor (known as a Super-capacitor), rechargeable and non-rechargeable electrochemical cells or a nuclear cell. In the case of a Super-capacitor or a rechargeable cell, the power source is periodically recharged by an external Radio Frequency Transmitter via inductive coupling in a manner known to the art. Often the Implantable medical device in these medical devices is driven by a microcontroller having a minimum operating voltage of approximately 2.2 volts. Once this minimum voltage is reached the device ceases to deliver medical therapy.

The present invention provides a method and circuitry for utilizing the remaining charge by converting a low power source voltage to a new constant value higher than the minimum operating voltage. This in effect extends the operating time of the medical device by "squeezing" more charge out of the power source.

Therefore, it is an object of the present invention to provide: (1) circuitry for sensing when the power source voltage reaches a low level which is close to the minimum operating voltage, (2) circuitry for activating a DC to DC Converter upon sensing a low voltage level, the output of the DC to DC Converter supplying a constant voltage higher than the minimum operating voltage, (3) circuitry for disconnecting the power supply inputs of an implantable medical device from the power source and connecting them to the DC to DC Converter output, (4) circuitry for shutting-down the DC to DC converter upon the power source reaching a high voltage level during recharging of the power source, and (5) circuitry for disconnecting the power supply inputs of the implantable medical device from the DC to DC Converter and reconnecting them to the power source.

Thus, according to the present invention there is provided a power supply comprising:

a power source for storing or generating electrical energy;

sensing circuitry for sensing when the voltage on the power source is above or below a certain level;

a DC-DC converter coupled to the power source;

switching circuitry coupled to the sensing circuitry and operable to connect the DC-DC converter to an output load and disconnect the power source from the output load when the voltage on the power source falls below a certain level and for connecting the power source to the output load and disconnecting the DC-DC converter from the output load when the voltage on the power source rises above a certain level;

means for activating the DC to DC Converter when the voltage on the power source falls below a certain level;

means for shutting down the DC to DC Converter when the voltage on the power source rises above a certain level.

Further according to the present invention, there is provided a method for extending the operating time of an implantable medical device including the steps of:

sensing when the voltage level on the power source is below or above a predetermined level;

producing a first logic signal when the voltage on the power source falls below a certain level and producing a second logic signal when the voltage on the power source is above a certain level;

providing a DC to DC converter coupled to the output of the power source;

activating the DC to DC Converter when the first logic signal is produced;

shutting down the DC to DC Converter when the second logic signal is produced;

switching the connections to an output load from the power source to the DC-DC converter when the first logic signal is produced; and connecting the power source to an output load and disconnecting the DC-DC converter from the output load when the second logic signal is produced.

Typically, the power source is mounted inside an implantable medical device, e.g. a neural stimulator, a pacemaker, a defibrillator or a drug infusion pump, to name a few.

BRIEF DESCRIPTION OF THE DRAWINGS

FIG. 1A illustrates the usable capacity in mA/hrs with and without the circuitry of the present invention.

FIG. 1B illustrates the operating time in months of a neural stimulator programmed to typical stimulation values with and without the circuitry of the present invention.

FIG. 2 illustrates the operating hours of a fully charged neural stimulator programmed to typical stimulation values with and without the circuitry of the present invention.

DESCRIPTION OF THE PREFERRED EMBODIMENT(S)

Figure 1A:
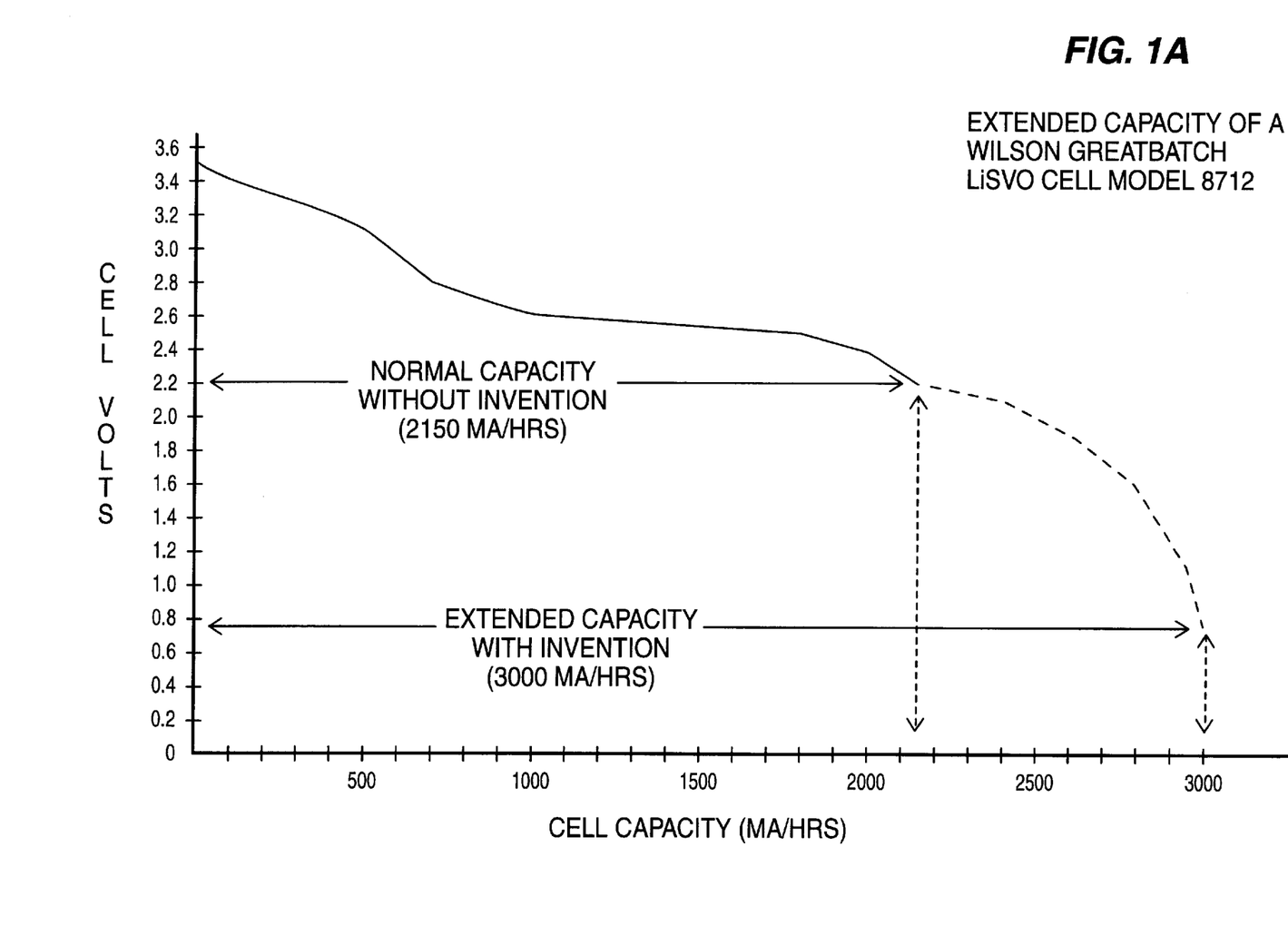
FIG. 1A is a graphic representation of the voltage profile of a Lithium Silver Vanadium Oxide cell commonly used in implantable neural stimulators and defibrillators.

Referring now to FIG. 1A, there is illustrated therein a graphic representation of the voltage profile of a Lithium Silver Vanadium Oxide cell commonly used in implantable neural stimulators and defibrillators.

FIG. 1A illustrates the usable capacity in mA/hrs with and without the circuitry of the present invention. Note that the invention increases the usable capacity from 2,150 mA/hrs to 3,000 mA/hrs, providing approximately a 40% increase.

Figure 1B:
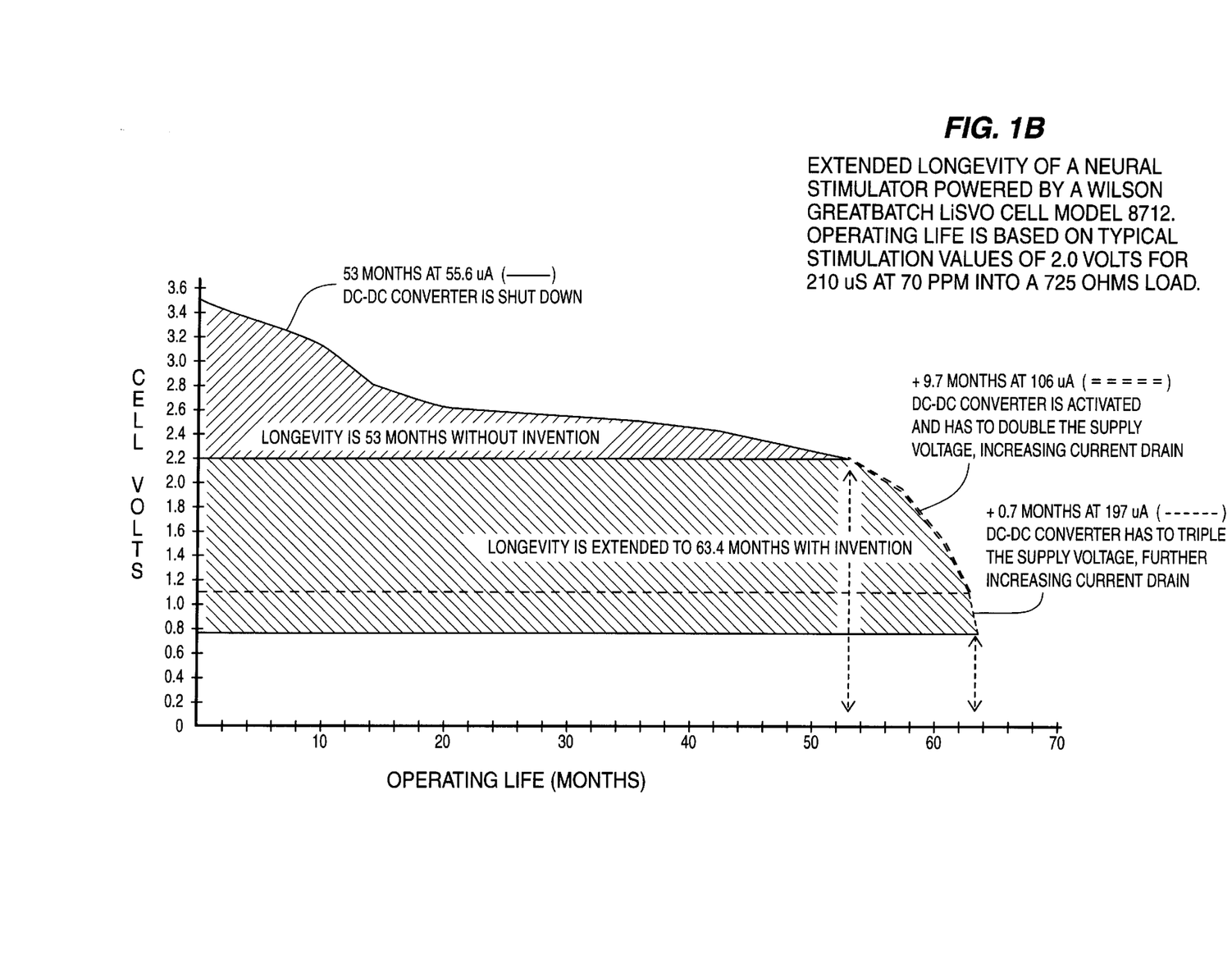
FIG. 1B is a graphic representation of the voltage profile of the same Lithium Silver Vanadium Oxide cell as modified by the circuitry of the present invention.

Unfortunately, FIG. 1B illustrates that the 40% increase in cell capacity does not translates into a 40% increase in operating time since activating the DC to DC converter 34 (FIGS. 4A and 4B) increases the current consumption significantly.

FIG. 1B illustrates the operating months, with and without the circuitry of the present invention, for a typical neural stimulator powered a lithium cell. It shows that without this invention the operating time is approximately 53 months, and that the operating time is extended to approximately 63.4 months by the invention (a 19.6% increase). Note the steeper discharge slope after 2.2 Volts. This is because for cell voltages between 2.2 and 1.1 volts the active DC to DC Converter will double the current consumption. Likewise, for cell voltages between 1.1 and down to 0.76, the active DC to DC Converter will quadruple the current consumption. Below 0.76 Volts the DC to DC Converter (and the implantable medical device) will cease to function.

Figure 2:
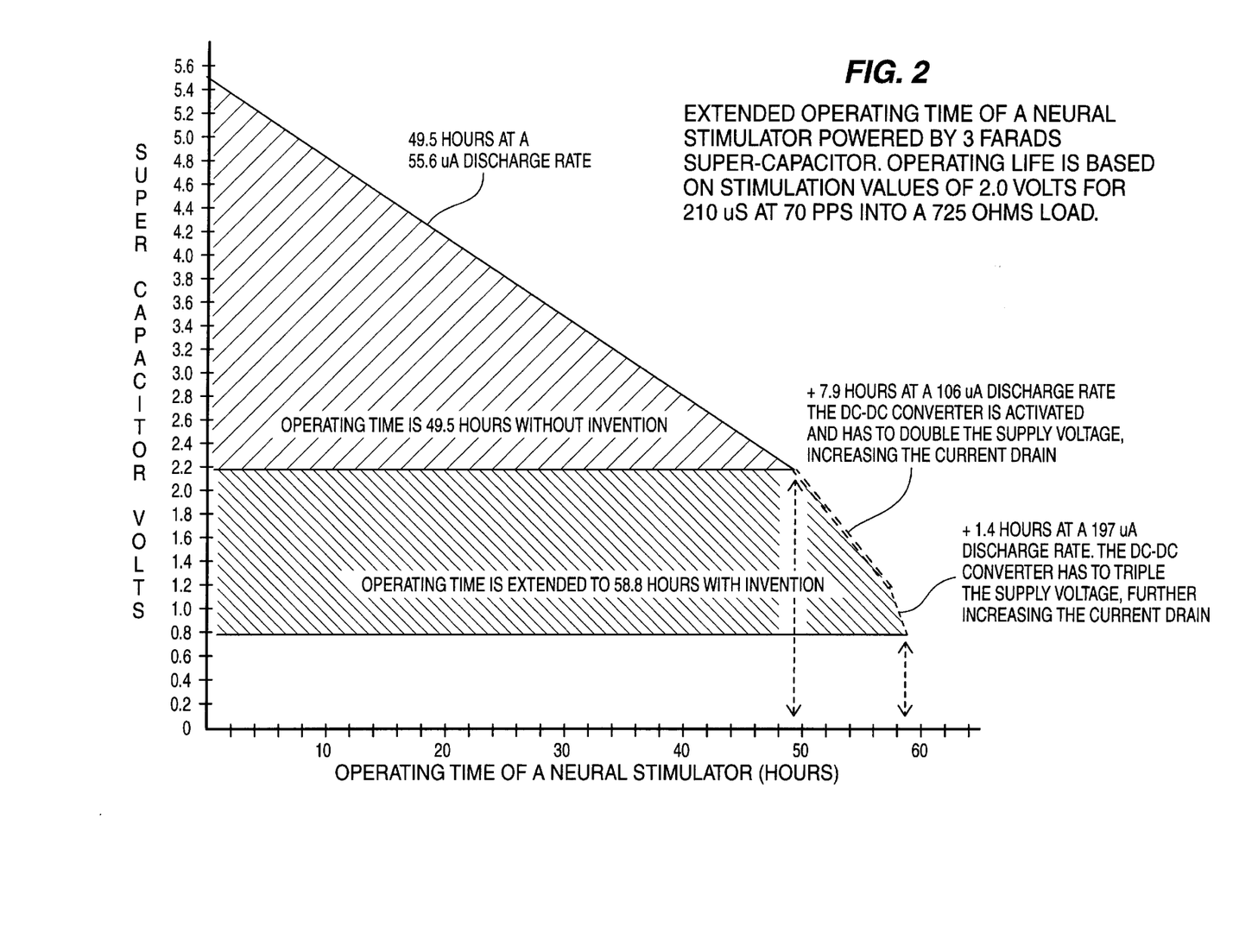
FIG. 2 is a graphic representation of the voltage profile of a 3 Farad Super-capacitor when used as the power source in an implantable neural stimulator.

Referring to FIG. 2, there is illustrated therein a graphic representation of the voltage profile of a 3 Farad Super-capacitor when used as the power source in an implantable neural stimulator. FIG. 2 illustrates the operating hours, with and without the circuitry of the present invention, of a fully charged neural stimulator programmed to typical stimulation values. Note that unlike most capacitive discharge curves which show an exponential decay, this curve is linear. This is because, for a typical neural stimulator, the stimulation voltage and the electrode impedance stay constant throughout the life of the device, therefore discharging the Super-capacitor at a constant rate. Also, note that there are three different discharge slopes: (1) a first slope for Super-capacitor voltages between 5.5 and 2.2 volts at 55.6 $\mu$A rate (solid line), (2) a second slope at 106 $\mu$A rate upon activation of the DC to DC Converter (double dash line) for Super-capacitor voltages between 2.2 and 1.1 Volts, and (3) a third slope at 197 $\mu$A rate for Super-capacitor voltages between 1.1 and 0.73 Volts (single dash line).

Figure 3:
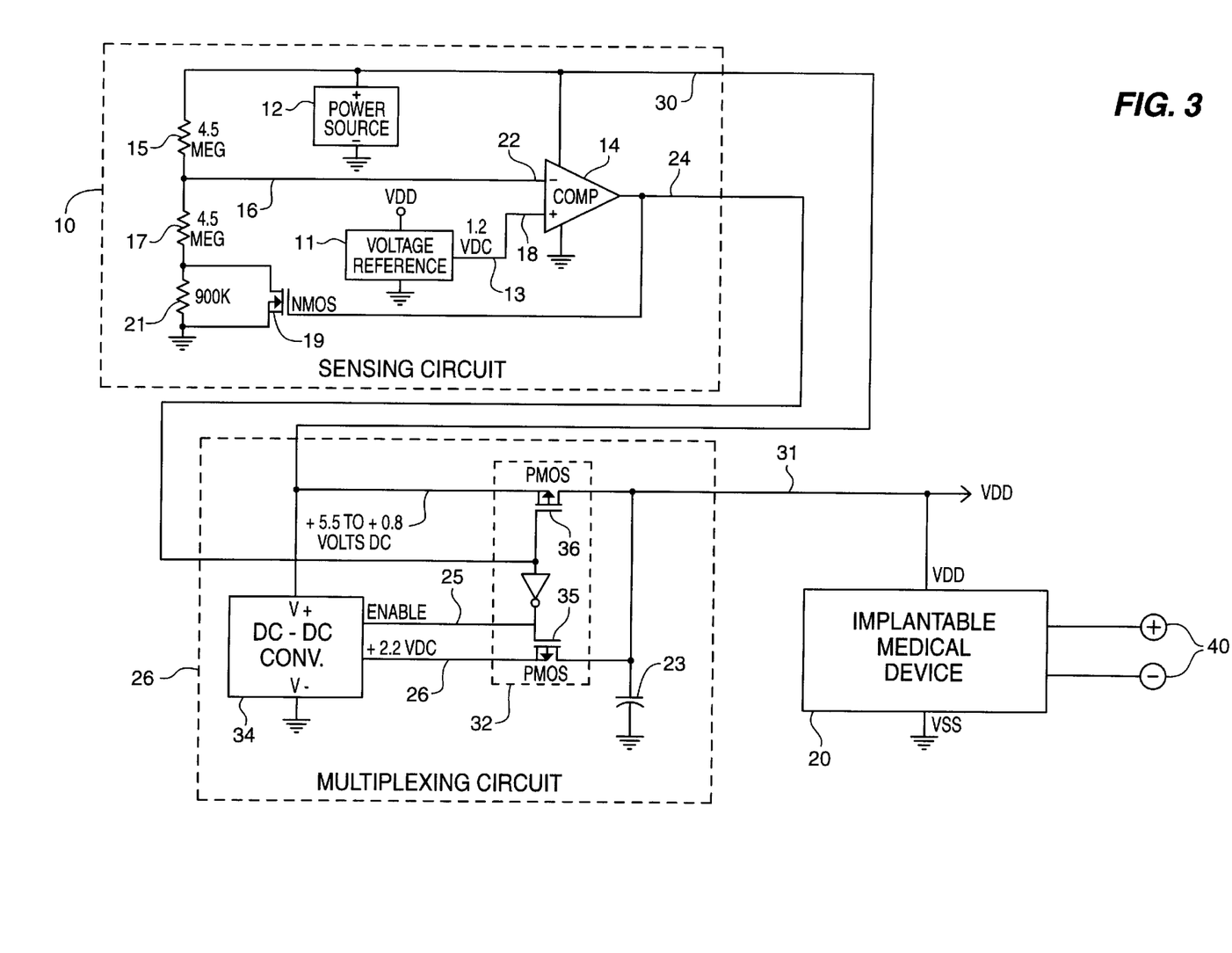
FIG. 3 is a block schematic circuit diagram of a "Sensing Circuit" for sensing a low voltage level on a power source, and of a "Multiplexing Circuit" utilizing transistors for connecting and disconnecting the input power leads of an implantable medical device to either the power source or to a DC-DC converter.

Referring now to FIG. 3, there is illustrated therein a block schematic circuit diagram for a "Sensing Circuit" 10 used to sense a "low" voltage level on a power source 12 which may be a Super-capacitor, an electrochemical cell (rechargeable and non-rechargeable), or nuclear cell. The sensing circuit 10 comprises a comparator 14 which has a tracking voltage 16 at a negative input 18 of the comparator 14 and a reference voltage 13 which is connected to the positive input of the comparator 14. The value of the tracking voltage is set to a fraction of the voltage produced by the power source 12 via a junction at resistor 15 and the series combination of resistors 17 and 21. Voltage reference 11 generates reference voltage 13 which is connected to the positive input of comparator 14. When the negative input 22 to the comparator 14 drops below the reference voltage 13, an output 24 of the comparator 14 will switch "high". When the negative input 22 to the comparator 14 raises above the reference voltage 13, the output 24 of the comparator 14 will switch "low". Voltage reference 11 is a "band-gap" type known to the art which produces a steady 1.2 volts and is insensitive to variations in temperature and supply voltage. In this example, the implantable medical device delivers stimulation pulses between electrodes 40 such as in a neural stimulator, a cardiac pacemaker or a cardiac defibrillator.

Also, in FIG.3, there is illustrated a block schematic circuit diagram for a "Multiplexing Circuit" 26 used to connect a set of power inputs 28 and 30 to an electrical switching circuit 32 controlled by sensing circuit 10 for powering the implantable medical device 20, from either power source 12 or from DC to DC converter 34. In FIG. 3 the switching circuit 32 comprises transistors 36 and 38, while in FIG. 4 the switching circuit 32 comprises Schottky diodes 39 and 41.

Referring to FIG. 3, when the output 24 of the comparator 14 is low, a transistor 36 of the switching circuit 32 connects power source 12 to the implantable medical device 20 and transistor 38 disconnects the implantable medical device 20 from output 28 of DC to DC Converter 34.

When the output 24 of the comparator 14 is high, transistor 38 is switched on to connect output 28 of DC to DC converter 34 to the implantable medical device 20 and transistor 36 is switched off to disconnect the implantable medical device from the power source 12.

When the output 24 of the comparator 14 is high, the enabling line 25 for the DC to DC Converter 34 will be low, activating the DC to DC Converter 34.

Figure 4:
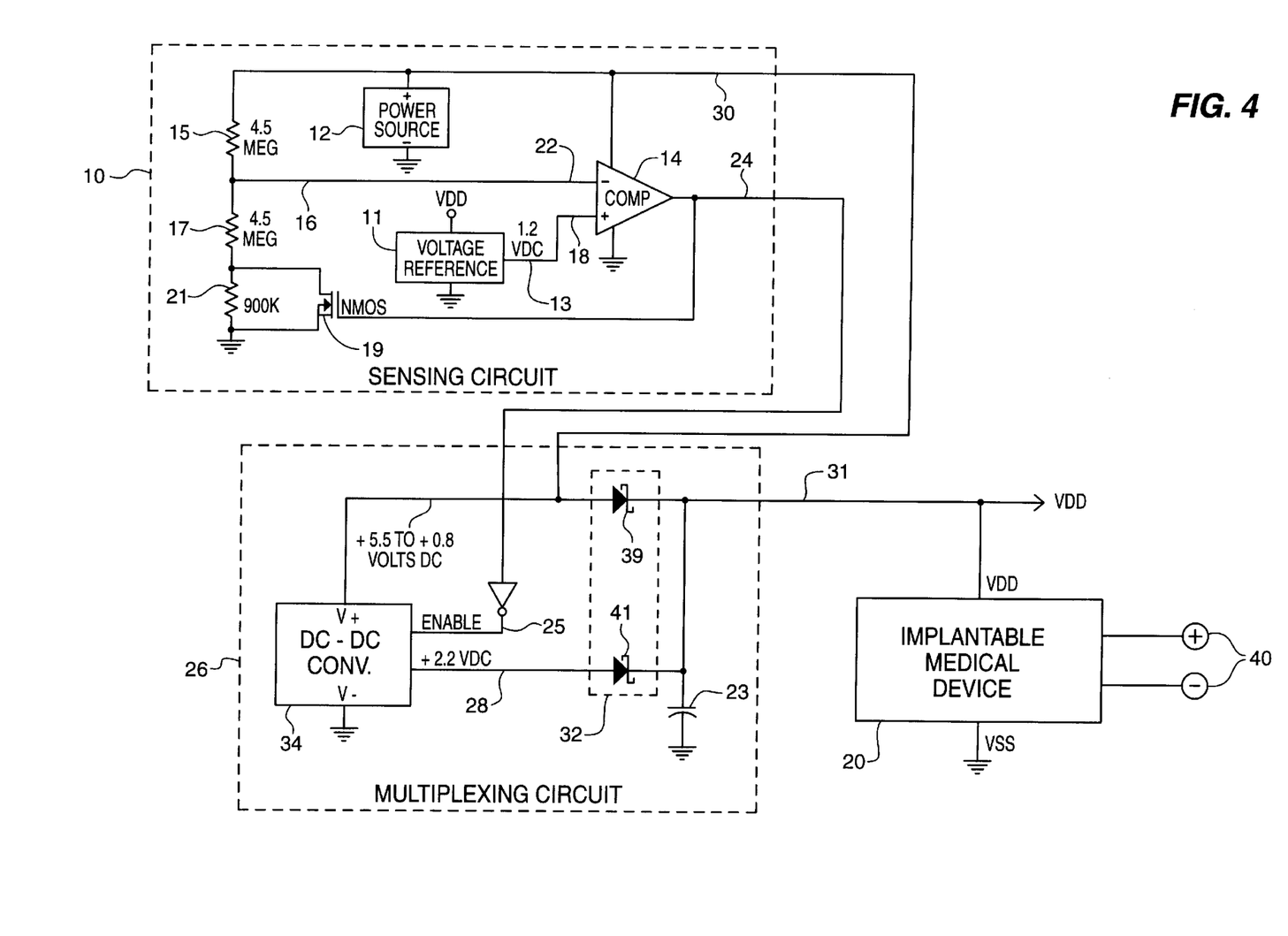
FIG. 4 is block schematic circuit diagram incorporating the same "Sensing Circuit" utilized in FIG. 3 but employing Schottky diodes (instead of transistors) in the "Multiplexing Circuit" for connecting and disconnecting the input power leads of the implantable medical device to either the power source or to a DC-DC converter.

Referring now to FIG. 4, when the voltage of the power source is above 2.2 volts, output 24 of the comparator 14 will switch low shutting down the DC to DC Converter. Schottky diode 39 of the switching circuit 32 becomes forward biased, connecting power source 12 to the implantable medical device 20. Schottky diode 41 is reverse biased disconnecting the implantable medical device 20 from the DC to DC Converter 34.

When the voltage of the power source is at or below 2.2 volts, output 24 of the comparator 14 will switch high activating the DC to DC Converter. Schottky diode 41 becomes forward biased connecting output 28 of the DC to DC converter 34 to the implantable medical device 20. Schottky diode 39 becomes reverse biased disconnecting the implantable medical device from the power source 12.

Figure 5:
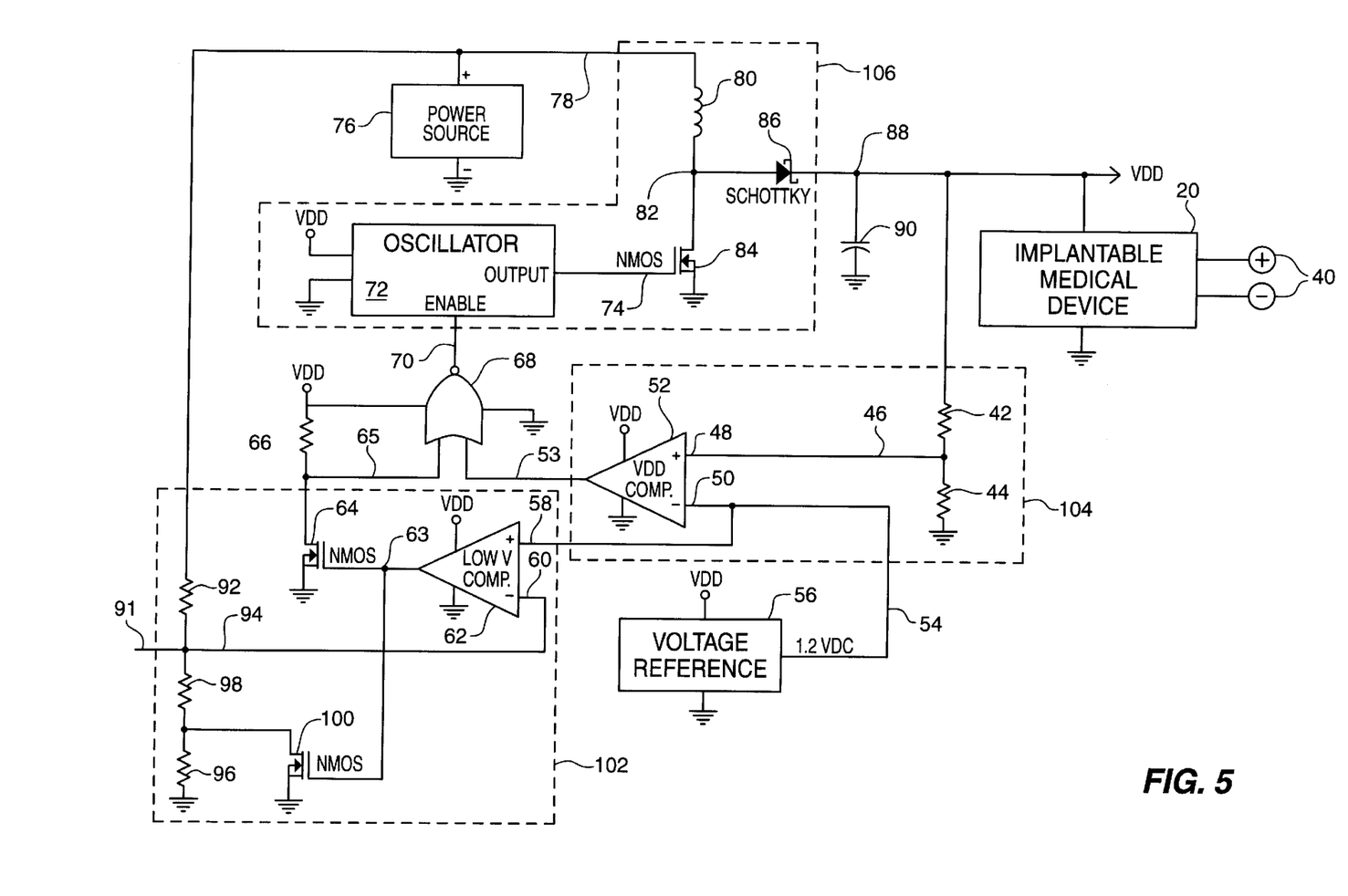
FIG. 5 is block schematic circuit diagram of an inductive type DC to DC Converter utilizing a single Schottky diode in series with a power inductor for connecting and disconnecting the input power leads of the implantable medical device to either the power source or to a DC-DC converter.

Referring now to FIG. 5, there is illustrated therein, a block schematic circuit diagram for an inductive type DC to DC Converter incorporating a simpler means (than in FIGS. 3 and 4) for switching the output load from the power source to the output of the DC to DC Converter. Basically, the circuit comprises a "Power Source Sensing Circuit" 102, a "Charge Pump" 106, and a "VDD Sensing Circuit" 106. The "Power Source Sensing Circuit" 102 is used to sense a "low" voltage level on a power source 76 which may be a Super-capacitor, an electrochemical cell (rechargeable and non-rechargeable), or nuclear cell. The "Inductive Charge Pump" 106 is used to maintain a voltage level of 2.2 volts on a capacitor 90 which becomes the VDD supply to the implantable medical device when the voltage on power source 76 drops below 2.2 volts. The "VDD Sensing Circuit" 104 is used to activate "Charge Pump" 106 when the voltage at capacitor 90 drops below 2.2 volts, and to shut down "Charge Pump" 106 when the voltage at capacitor 90 reaches 2.2 volts.

"Power Source Sensing Circuit" 102 comprises a comparator 62 which has a tracking voltage 94 at a negative input 60 of the comparator 62 and reference voltage 54 which is connected to the positive input 58 of the comparator 62. The value of the tracking voltage is set to a fraction of the voltage produced by power source 76 via the junction 91 at resistor 92 and the series combination of resistors 96 and 98. When the negative input 60 to the comparator 62 drops below the reference voltage 54, an output 63 of the comparator 62 will switch "high". When the negative input 60 to the comparator 62 raises above the reference voltage 54, the output 63 of the comparator 62 will switch "low".

Voltage reference 56 is a "band-gap" type known to the art which produces a steady 1.2 volts and is insensitive to variations in temperature and supply voltage. In this example, the implantable medical device delivers stimulation pulses between electrodes 40 such as in a neural stimulator, a cardiac pacemaker or a cardiac defibrillator. When the output 63 of comparator 62 switches "high", transistor 100 conducts and shorts out resistor 98 providing some hysteresis which prevents the output 63 of comparator 58 from oscillating. Also, transistor 64 will conduct pulling line 65 "low". Sense comparator 52 is used to sense the VDD voltage being supplied to the implantable medical device 20 via the voltage at the junction of resistors 42 and 44.

When the VDD voltage on capacitor 90 drops below a certain minimum level, output 53 of comparator 52 will switch "low", placing a second "low" on NOR gate 68. This will cause line 70 to switch "High" activating oscillator 72. The output 74 of oscillator 72 will start to generate an square wave causing transistor 84 to alternatively switch on and off during each cycle of the square wave. During each "on time" of transistor 84 and inductor 80 will saturate. During each "off time" of transistor 84 the electric field on inductor 80 will collapse resulting in a self-induced positive voltage which will forward bias diode 86 and inject a positive charge into capacitor 90. When the voltage on capacitor 90 reaches about 2.2 volts, the output 53 of comparator 52 will switch "high" and the output 70 of NOR gate 68 will switch "low" shutting down oscillator 72 and transistor 84. Since the voltage on power source 76 is below 2.2 volts, diode 86 will become reverse biased, disconnecting power source 76 from the VDD input to the implantable medical device. As the voltage on capacitor 90 drops below 2.2 volts, oscillator 72 is again enabled to recharge capacitor 90. In this fashion, oscillator 72 is alternatively switched "on" and "off" as required to maintain 2.2 volts at capacitor 90. When the voltage on the power source reaches approximately 0.8 volts, the thresholds for the CMOS circuitry cannot be reached and the DC to DC Converter ceases to operate.

It will be understood that various forms of switching circuits can be used and that the use of transistors 36 and 38 or Schottky diodes 39 and 41 is for illustrative purposes only.

The circuitry described above can be used to extend the operating life of any capacitive, electrochemical or nuclear power source or it can be used as a back up system. As stated previously, it is ideal for use with a power source in an implantable medical device.

From the foregoing description, it will be apparent that the method and circuitry for extending the operating time for a power source of the present invention has a number of advantages, some of which have been described above and others of which are inherent in the invention. Also, it will be understood that modifications can be made to the invention without departing from the teachings of the invention. Accordingly, the scope of the invention is only to be limited by the accompanying claims.

We claim:

1. An implantable medical device having a power supply comprising:

power source means for storing or generating electrical energy selected essentially from the class comprising: a large value capacitor, an electrochemical cell (rechargeable or non-rechargeable), or a nuclear cell;

sensing means for sensing when the voltage on said power source means is above or below a certain level;

a DC-DC converter coupled to said power source means;

switching means coupled to said sensing means and operable to connect said DC-DC converter to an output load and disconnect said power source means from the output load when the voltage on said power source means falls below a certain level and for connecting said power source means to the output load and disconnecting said DC-DC converter from the output load when the voltage on said power source means rises above a certain level;

means for activating said DC to DC Converter when the voltage on said power source falls below a certain level; and means for shutting down said DC to DC Converter when the voltage on said power source rises above a certain level.

2. The implantable medical device of claim 1 wherein said sensing means comprises a comparator having a positive input coupled to a voltage reference and a negative input coupled to a voltage source representing a fraction of the voltage on said power source means.

3. The implantable medical device of claim 2 wherein said comparator outputs a logic high when the voltage on said power source means falls below a certain level and outputs logic low when the voltage on said power source means exceeds a certain level.

4. The implantable medical device of claim 1 wherein said switching means comprises a first electronic switch for closing a first circuit and opening a second circuit when said switching means receives a logic high and a second electronic switch for opening said first circuit and closing said second circuit when said switching means receives a logic low signal.

5. The implantable medical device of claim 4 wherein said electronic switch means comprises two PMOS transistors.

6. The implantable medical device of claim 4 wherein said electronic switch means comprises two Schottky diodes.

7. The implantable medical device of claim 1 wherein said switching means is defined by an inductor and transistor connected in series between said power source means and a common or ground for said power supply and an oscillator connected to a base of said transistor and receiving an input from said sensing means; and wherein a junction between said inductor and transistor being coupled through a diode to said implantable medical device.

8. The implantable medical device of claim 7 including a storage capacitor connected to the output and said diode being a Schottky diode.

9. A power supply comprising:

capacitive, electrochemical or nuclear means for storing or generating electrical energy;

sensing means for sensing when the voltage on said power source means is above or below a certain level;

a DC-DC converter coupled to said power source means;

switching means coupled to said sensing means and operable to connect said DC-DC converter to an output load and disconnect said power source means from the output load when the voltage on said power source means falls below a certain level and for connecting said power source means to the output load and disconnecting said DC-DC converter from the output load when the voltage on said power source means rises above a certain level;

activating means for activating said DC to DC Converter when the voltage on said power source falls below a certain level; and shutting down means for shutting down said DC to DC Converter when the voltage on said power source rises above a certain level.

10. The power supply of claim 9 wherein said sensing means comprises a comparator having a positive input coupled to a voltage reference and a negative input coupled to a voltage source representative of the voltage on said power source means.

11. The power supply of claim 10 wherein said comparator outputs a logic high when the voltage on said power source means falls below a certain level and outputs logic low when the voltage on said power source means exceeds a certain level.

12. The power supply of claim 9 wherein said switching means comprises an electronic switch for closing a first circuit and opening a second circuit when said electronic switching circuit receives a logic high signal and for opening said first circuit and closing said second circuit when said electronic switching circuit receives a logic low signal.

13. The power supply of claim 9 wherein said switching means comprises two PMOS transistors.

14. The power supply of claim 9 wherein said switching means comprises two Schottky diodes.

15. The power supply means of claim 9 wherein said switching means is defined by an inductor and transistor connected in series between said power source means and a common or ground for said power supply and an oscillator connected to a base of said transistor and receiving an input from said sensing means; and wherein a junction between said inductor and transistor being coupled through a diode to said implantable medical device.

16. The power supply of claim 9 including a storage capacitor connected to the output of said diode and said diode being a Schottky diode.

17. A method for extending the operating time of a capacitive or electrochemical power source including the steps of:

sensing when the voltage level on said power source is below or above a certain level;

producing a first logic signal when the voltage on said power source falls below a certain level and producing a second logic signal when the voltage on said power source is above a certain level;

providing a DC-DC converter coupled to the output of said power source;

switching the connections to an output load from said power source to the DC-DC converter when a first logic signal is produced; and connecting said power source to an output load the disconnecting the DC-DC converter from the output load when a second logic signal is produced;

activating said DC to DC Converter when said first logic signal is produced; and shutting down said DC to DC Converter when said second logic signal is produced.

18. A method for extending the operating time of a capacitive, electrochemical or nuclear power source in an implantable medical device including the steps of:

sensing when the voltage level on said power source is below or above a certain level;

producing a first logic signal when the voltage on said power source falls below a certain level and producing a second logic signal when the voltage on said power source is above a certain level;

providing a DC-DC converter coupled to the output of said power source;

switching the connections to an output load from said power source to the DC-DC converter when a first logic signal is produced; and connecting said power source to an output load and disconnecting the DC-DC converter from the output load when a second logic signal is produced;

activating said DC to DC Converter when said first logic signal is produced; and shutting down said DC to DC Converter when said second logic signal is produced.

* * * * *